United States Patent
Zhang et al.

(10) Patent No.: US 12,299,546 B2
(45) Date of Patent: May 13, 2025

(54) MONITORING MOVEABLE ENTITIES IN A PREDETERMINED AREA

(71) Applicant: KONINKLIJKE PHILIPS N.V., Eindhoven (NL)

(72) Inventors: Ming Zhang, Eindhoven (NL); Supriyo Chatterjea, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1041 days.

(21) Appl. No.: 17/261,604

(22) PCT Filed: Sep. 6, 2019

(86) PCT No.: PCT/EP2019/073801
§ 371 (c)(1),
(2) Date: Jan. 20, 2021

(87) PCT Pub. No.: WO2020/049141
PCT Pub. Date: Mar. 12, 2020

(65) Prior Publication Data
US 2021/0264316 A1 Aug. 26, 2021

(30) Foreign Application Priority Data
Sep. 6, 2018 (EP) .................................... 18193015

(51) Int. Cl.
*G06N 20/00* (2019.01)
*G16H 40/20* (2018.01)
*G16H 50/20* (2018.01)

(52) U.S. Cl.
CPC ............. *G06N 20/00* (2019.01); *G16H 40/20* (2018.01); *G16H 50/20* (2018.01)

(58) Field of Classification Search
CPC ........................... G06N 20/00; F21V 23/0471
USPC ............................ 706/12; 700/276; 705/400
See application file for complete search history.

(56) References Cited

U.S. PATENT DOCUMENTS

| | | | | |
|---|---|---|---|---|
| 9,275,483 | B2 * | 3/2016 | Chu | G06T 11/206 |
| 9,689,583 | B2 * | 6/2017 | Katuri | H04L 67/125 |
| 11,808,580 | B1 * | 11/2023 | Ebrahimi Afrouzi | G01S 17/89 |
| 12,092,467 | B1 * | 9/2024 | Ebrahimi Afrouzi | G01C 21/32 |
| 2009/0024491 | A1 | 1/2009 | Choubey | |
| 2009/0327102 | A1 | 12/2009 | Kalra et al. | |

(Continued)

FOREIGN PATENT DOCUMENTS

| | | | | |
|---|---|---|---|---|
| AU | 2015203026 A1 * | 7/2015 | | F21V 23/0471 |
| CN | 105910225 A | 8/2016 | | |
| EP | 3621002 A1 * | 3/2020 | | G06N 20/00 |

OTHER PUBLICATIONS

International Search Report for PCT/EP2019/073801 dated Sep. 6, 2019.

(Continued)

*Primary Examiner* — Ruay Ho

(57) ABSTRACT

A method and system that enables a computer to determine a cause of occupancy of a predetermined area using real-time location information. The real-time location information is processed to determine occupancy information of each of a plurality of zones of the predetermined area. The (combined) occupancy information is processed using a machine-learning model to predict an occupancy cause of the predetermined zones of the predetermined area.

12 Claims, 3 Drawing Sheets

(56) References Cited

U.S. PATENT DOCUMENTS

| | | | |
|---|---|---|---|
| 2011/0184886 A1* | 7/2011 | Shoham | G06Q 30/0283 |
| | | | 705/400 |
| 2017/0177807 A1 | 6/2017 | Fabian | |
| 2017/0243488 A1 | 8/2017 | Ermakov et al. | |
| 2017/0337791 A1* | 11/2017 | Gordon-Carroll | H04W 4/023 |
| 2018/0038949 A1* | 2/2018 | Cha | G01S 13/56 |
| 2018/0144599 A1 | 5/2018 | Chen et al. | |
| 2019/0135317 A1* | 5/2019 | Hilleary | G01S 13/931 |
| 2019/0387365 A1 | 12/2019 | Spruyt et al. | |
| 2022/0124531 A1* | 4/2022 | Miao | H04B 17/345 |
| 2023/0152652 A1* | 5/2023 | Trikha | H10K 59/65 |
| | | | 700/276 |

OTHER PUBLICATIONS

Bratt, J.H. et al., "A comparison of four approaches for measuring clinician time use." Health Policy Plan, 14 (4):374-381, Dec. 1999.

Jones, T.L. et al., "Can real time location system technology (RTLS) provide useful estimates of time use by nursing personnel?" Res Nurs Health, 37(1):75-84, Feb. 2014.

Hunting, K.L. et al., "Validity assessment of self-reported construction tasks." J Occup Environ Hyg, 7(5):307-314, May 2010.

Donaldson S.I. et al., Understanding self-report bias in organizational behavior research. Journal of Business and Psychology, 17(2):245-260, 2002.

\* cited by examiner

MONITORING MOVEABLE ENTITIES IN A PREDETERMINED AREA

CROSS-REFERENCE TO PRIOR APPLICATIONS

This application is the U.S. National Phase application under 35 U.S.C. § 371 of International Application No. PCT/EP2019/073801, filed on Sep. 6, 2019, which claims the benefit of European Patent Application No. 18193015.7, filed on Sep. 6, 2018. These applications are hereby incorporated by reference herein.

FIELD OF THE INVENTION

The present invention relates to a field of monitoring movable entities, and in particular to the field of determining causes for occupancy of a predetermined area.

BACKGROUND OF THE INVENTION

In the medical field, there is an increasing desire to track and/or monitor the reasons why different zones of a predetermined area (such as a hospital or clinic) are being occupied. This information is important for optimizing hospital workflows and for identifying potentially inefficient operational practices.

One known method of identifying a cause of occupancy of an area is for a dedicated observer to monitor the area, e.g. in person or using CCTV, and identify events occurring within the area. Identified events can be considered causes of the different zones of the area being occupied. Such a method is overt and intrusive, as well as requiring additional overhead (such as substantial additional members of staff and/or equipment) and therefore costly.

Another known method is to require members of staff and/or other users of the area to log their reasons for occupying one or more zones of the area. However, such methods are inaccurate, e.g. due to non-compliance or forgetfulness, and add a significant burden to users of the predetermined area.

It will be clear that there is therefore a desire for an automated and low-cost method of determining a cause of occupancy of a predetermined area.

SUMMARY OF THE INVENTION

The invention is defined by the claims.

According to examples in accordance with an aspect of the invention, there is provided a computer-implemented method of monitoring moveable entities within a predetermined area. The method comprises: obtaining a stream of real-time location, RTL, information identifying current locations of movable entities within the predetermined area; processing the stream of real-time location information to generate occupancy information of each of a plurality of predetermined zones of the predetermined area; and processing the occupancy information using a machine-learning model to thereby determine one or more occupancy causes, each occupancy cause indicating the occurrence of a predetermined event within one or more predetermined zones, wherein the machine-learning model defines a relationship between occupancy information and occupancy causes.

The present invention recognizes that there is a relationship between locations of movable entities and the occurrence of events within zones occupied by the movable entities. In other words, it has been recognized that the occurrence of a predetermined event in a predetermined area (formed of zones) can be derived by monitoring the locations of moveable entities about the predetermined area.

The proposed embodiments provide methods for enabling a mapping between real-time locations of moveable entities and predetermined events associated with the moveable entities. This advantageously provides a new input methodology for identifying an occupancy cause of a predetermined area, being a predetermined event occurring within the predetermined area.

In particular, the present invention recognizes that occupancy information of zones of the predetermined area can be used to identify or predict the occurrence of a predetermined event of one or more zones (i.e. an event explaining why a particular zone or particular zones are occupied by one or more moveable entities).

In particular, the proposed method uses the real time locations of movable entities to derive occupancy information of each of a plurality of predetermined zones. This occupancy information is then processed, using a machine-learning model, to identify occupancy causes of the plurality of zones.

In this way, a machine-learning model is applied to occupancy information of a plurality of zones to predict one or more occupancy causes of the predetermined area. Thus, a machine-learning model can map occupancy information of a plurality of zones to a cause of occupancy. It has been advantageously recognized that a machine-learning model can be trained to correlate occupancy information of a plurality of zones with predetermined events occurring within a zone or zones.

As used herein, an "occupancy cause" is data or information indicating the occurrence of an event within one or more zones (occupied by the moveable entities), such as establishing identifying events that require attendance of particular moveable entities or result in particular movements of the moveable entities. Thus, an occupancy cause may be the occurrence of an instance of a predetermined event that results in one or more certain zones being occupied by moveable entities. The occupancy cause thereby provides a reason why one or more zones are occupied, i.e. the purpose behind the occupation of one or more zones.

In particular embodiments, the occupancy cause may indicate the occurrence of an event occurring within a specific or single zone. In other words, the step of determining one or more occupancy causes may comprise identifying the occurrence of a predetermined event occurring within a specific (single) zone. This provides more precise, specific and relevant information on the occurrence of an event.

The present invention provides a method of identifying the occurrence of a predetermined event (or events) within one or more predetermined zones. This enables the occurrence of a (in)correct or (un)expected sequence of events (e.g. by comparing identified events to a schedule). The occurrence of incorrect events could indicate an incorrect operating procedure. In a clinical environment, this could be used to alert the occurrence of an incorrect medical procedure, which would significantly affect a subject's health. In a manufacturing environment, this could be used to detect the occurrence of an incorrect or unscheduled manufacturing step, which would lead to an incorrect product being manufactured.

In other words, detecting the occurrence of a predetermined event could, for example, be used to prevent incorrect events from harming a patient in a clinical environment (such as an incorrect or unnecessary surgery) or an undesirable processing step within a manufacturing environment (such as an incorrect coating, cutting or metal-stamping procedure). There is therefore a technical incentive to provide and improve identification of predetermined events within one or more zones.

Similarly, the proposed method can also ensure that desirable events do take place, for example, to ensure that proper hygiene procedures (e.g. cleaning events) are performed prior to a surgery event or to ensure that the correct resources (e.g. personnel or equipment) are available before the next phase (i.e. next event) of a surgical procedure.

Moveable entities here include patients, clinicians, health care professionals, pieces of (medical) equipment (such as a bed, a defibrillator, a ventilation machine or anesthesiology equipment) and so on. Typically, the moveable entities are clinically-relevant movable entities. Thus, moveable entities may comprise movable (non-human) assets and/or persons/individuals. Thus, a "moveable entity" may be alternatively labelled a "movable asset".

Some embodiments of the present invention thereby provide a data processing architecture that allows a computer to be adapted for identifying a cause of occupancy of a predetermined area using real-time location information. In other words, the proposed embodiments enable automatic monitoring of a cause of occupancy of the predetermined area.

This enables occupancy causes, such as the occurrence of "collaborative events" as later described, to be determined in a low-cost, sustainable, long-term, unobtrusive, accurate and private manner when compared to traditional ways (e.g. interviews or observers).

Preferably, the occupancy information comprises non-binary information. In particular, the occupancy information may provide additional information beyond merely indicating whether or not a zone is occupied. It has been recognized that real-time location (RTL) information can be used to create information having greater granularity than a simple binary indicator. Non-binary information can thereby provide more contextual information that helps improve determination of an occupancy cause. Some examples of suitable non-binary information for the occupancy information will be hereafter provided.

The computer-implemented method may be adapted wherein: the occupancy information indicates a number of moveable entities in each of the plurality of predetermined zones of the predetermined area; and the machine-learning model defines a relationship between a number of moveable entities within each predetermined zone and occupancy causes.

Embodiments recognize that a number of moveable entities within each zone can define the cause of a zone or zones being occupied. The machine-learning model can therefore be adapted to map a number of occupants in each zone to an event occurring within one or more zones. This advantageously enables predetermined events to be identified.

In some embodiments, the computer-implemented method comprises determining one or more roles of each at least one movable entity, wherein: the occupancy information indicates the one or more roles of each movable entity in each of the plurality of predetermined zones of the predetermined area; and the machine-learning model defines a relationship between the one or more roles of each moveable entity in each predetermined zone and occupancy causes.

Preferably, there are at least two different possible types of role or labels for the moveable entities, more preferably at least three different possible type, and even more preferably at least five different possible types. The more possible types, the greater the granularity of the occupancy information and thus the accuracy of the determined occupancy cause.

The role of moveable entities (e.g. identity or capabilities of a movable entity) can be used to help determine a reason for a zone being occupied by said moveable entities. Proposed embodiments recognize that a role or the capabilities of a moveable entity define the possible causes for those entities occupying particular zones.

By way of example, occupancy information may be obtained from a real-time locating information supplied by a real time location system (RTLS). The RTLS may be adapted to determine both a location of a movable entity and a role of the movable entity (e.g. by tracking the location of a moveable entity having a known role).

Thus, embodiments provide a technique for assessing a cause of occupancy based on roles and zonal locations of one or more movable entities in the predetermined area.

In more preferable embodiments, the computer-implemented method comprises determining one or more roles of each at least one moveable entity, wherein: the occupancy information indicates a number of moveable entities of each role within each of the plurality of predetermined zones of the predetermined area. The occupancy information may therefore indicate a total number of moveable entities of each role (or type) in each zone. Such an instance of occupancy information (i.e. at a single point in time or an average over a period of time) can be labelled an occupancy data entry. The occupancy data entry effectively comprises a histogram of roles and counts for a particular point or period of time.

Preferably, the step of processing the stream of real-time location information comprises generating, as the occupancy information, a sequence of occupancy data entries, each occupancy data entry indicating a number of moveable entities within each of the plurality of predetermined zones of the predetermined area at a single point in time; where each occupancy data entry is associated with a single point in time later than a previous occupancy data in the sequence of occupancy data entries, so that the overall sequence indicates a number of moveable entities within each of the plurality of predetermined zones over a period of time.

A sequence of occupancy data entries thereby indicates how the (zonal) position of each moveable entity changes over a period of time. Such an embodiment recognizes that the cause of an occupancy can be identified by monitoring how a moveable entity changes location (e.g. at what speed or by assessing destination and/or origin).

The machine-learning model may correspondingly be adapted to identify or derive a cause of occupancy by assessing how the moveable entities' location(s) changes over time (i.e. the sequence of movement).

Use of a sequence of occupancy data entries (e.g. snapshots of the location(s) of the at least one moveable entities) provides an intuitive and machine-processable mechanism for determining a cause of the occupancy of (one or more zones) of the predetermined area.

Even more preferably, each occupancy data entry indicates a number of moveable entities of each of predetermined number of roles in each predetermined zone at a single point in time.

In other words, the method may comprise determining one or more roles of each at least one movable entity, wherein the step of generating the sequence of occupancy data entries comprises generating a sequence of occupancy data entries wherein each occupancy data entry indicates a number of moveable entities of each role within each of the plurality of predetermined zones of the predetermined area at a single point in time.

Thus, an occupancy data entry can indicate, for each of the predetermined zones, a number of moveable entities of each of a plurality of different entity roles that occupy the predetermined zone at a particular point in time.

Thus, the machine-learning model may define a relationship between a sequence of occupancy data entries and one or more occupancy causes (i.e. one or more predetermined events).

In some embodiments, the occupancy information comprises a plurality of sequences of occupancy data entries and the step of processing the occupancy information comprises individually processing each sequence of occupancy data using a machine-learning model to thereby determine one or more occupancy causes.

Use of a plurality of sequences enables increased and/or more granular determination of different causes of occupancy, i.e. different predetermined events.

Preferably, the plurality of sequences forms a series of sequences; and each of the sequences in the series is associated with a period of time beginning at a later point in time than an immediately preceding sequence in the series of sequences.

Thus, a sequence or series of sequences may be obtained, where each sequence is temporally displaced from all other sequences in the series. This increases a period of time over which causes for an occupancy can be identified. Using a plurality of sequences also increases a precision at which causes can be identified.

Preferably, each sequence is associated with a time period of a predetermined length.

Optionally, each of the series of sequences may be associated with a period of time that overlaps a period of time associated with an immediately preceding sequence in the series of sequences.

By overlapping different sequences (in the series of sequences), it is less likely that a cause of occupancy is overlooked or not identified. This improves an accuracy of the methodology for determining a cause of occupancy of the predetermined area.

By way of example, without overlapping sequences—a predetermined event causing occupancy of a particular zone that spans a period of time that overlaps two consecutive sequences may be overlooked.

The method may comprise, after processing the steam of real-time location information, discarding the stream of real-time location information.

This improves a privacy of the movable entities, as specific information as to their whereabouts (i.e. real-time location) is discarded. This can also help improve a security of an area, as such information cannot subsequently be provided to a further system or user—thereby reducing unintentional leaking of information.

Preferably, determining the one or more occupancy causes comprises determining whether one or more predetermined events have occurred during a time during which the stream of real-time location, RTL, information is provided.

In other words, the machine-learning model may be adapted to map or associate occupancy information with one or more predetermined events. That is, the machine-learning model may aim to recognize the presence or influence of one or more predetermined events in the occupancy information.

Recognition of predetermined events is important to understanding the causes of occupancy of a predetermined area. In particular, it has been recognized that an event (e.g. such as a team meeting) may provide the reason for a zone of the predetermined area being occupied. By mapping occupancy information to one or more predetermined events, such reasons can therefore be easily identified.

According to examples in accordance with another aspect of the invention, there is provided a computer program comprising code means for implementing any previously described method when said program is run on a computer.

According to examples in accordance with another aspect of the invention, there is provided a system for monitoring moveable entities within a predetermined area. The system comprises: a stream receiving unit adapted to obtain a stream of real-time location, RTL, information identifying current locations of movable entities within the predetermined area; a processing unit adapted to process the stream of real-time location information to generate occupancy information of each of a plurality of predetermined zones of the predetermined area; and an occupancy cause identifying unit adapted to process the occupancy information using a machine-learning model to thereby determine one or more occupancy causes, each occupancy cause indicating the occurrence of a predetermined event within one or more predetermined zones, wherein the machine-learning model defines a relationship between occupancy information and occupancy causes.

The system may further comprise a role determining unit adapted to determine one or more roles of each at least one movable entity, wherein: the occupancy information indicates the one or more roles of each movable entity in each of the plurality of predetermined zones of the predetermined area; and the machine-learning model defines a relationship between the one or more roles of each moveable entity in each predetermined zone and occupancy causes.

Preferably, the processing unit is adapted to processing the stream of real-time location information to generate a sequence of occupancy data entries, each occupancy data entry indicating a number of moveable entities within each of the plurality of predetermined zones of the predetermined area at a single point in time.

In some embodiments, the system is adapted wherein the processing unit is adapted to generate a plurality of sequences of occupancy data entries; and the occupancy cause identifying unit is adapted to individually process each sequence of occupancy data in the plurality of sequences using a machine-learning model to thereby determine one or more occupancy causes.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
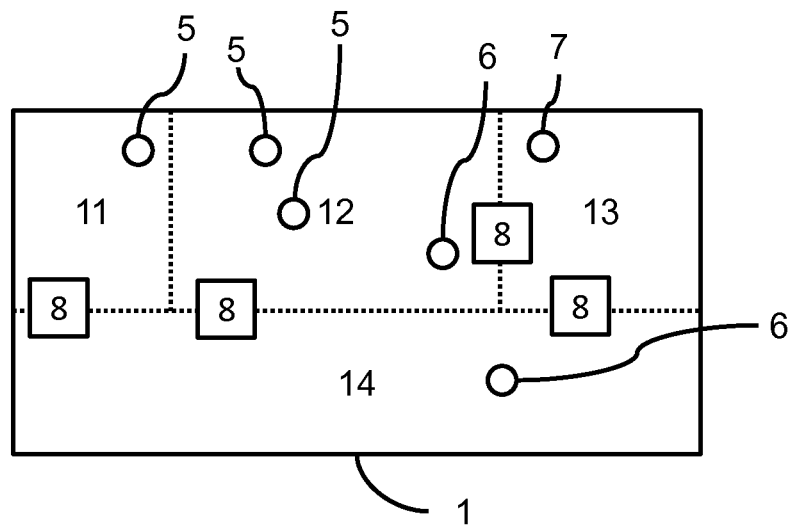
FIG. 1 illustrates a predetermined area suitable for being monitored by a method according to an embodiment.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

According to a concept of the invention, there is proposed a method and system that enables a computer to determine a cause of occupancy of a predetermined area using real-time location information. The real-time location information is processed to determine occupancy information of each of a plurality of zones of the predetermined area. The (combined) occupancy information is processed using a machine-learning model to predict an occupancy cause of the predetermined zones of the predetermined area.

Embodiments are at least partly based on the realization that real-time location information needs to be appropriately structured to be processed by a machine-learning model, and that such structures are not currently available. As such, by determining occupancy information for zones of the predetermined area, structure can be given to real-time location information to thereby allow detection of occupancy causes to take place.

Illustrative embodiments may, for example, be employed in hospital monitoring system to monitor and detect the occurrence of predetermined events within the hospital. The detection (or lack of detection) of a predetermined event could be used to generate an alert that indicates if a scheduled predetermined event is not taking place, thereby reducing the occurrence of unscheduled/incorrect events and/or missing scheduled events.

The present invention is described in the context of a clinical environment. However, embodiments may extend to other environments, such as industrial complexes, warehouses, or manufacturing plants.

FIG. 1 illustrates a snapshot of a predetermined area 1 that has been conceptually divided into a plurality of predetermined zones 11-14.

The predetermined area 1 may, for example, be a particular floor or area of a clinical building (e.g. hospital or clinic), or may represent the overall clinical building. Each zone 11-14 of the predetermined area can represent a different room of the clinical building. For example, a first zone 11 may represent a ward 11, a second zone 12 may represent an examination room 12, a third zone 13 may represent a control room 13 and a fourth zone 14 may represent a corridor 14.

One or more moveable entities 5, 6, 7, are distributed about the predetermined area. There may, as illustrated, be more than one type of moveable entity 5, 6, 7, where each type of moveable entity is associated with a different role or identity. For example, a first moveable entity 5 may be a nurse for the clinical setting, a second moveable entity 6 may be a physician for the clinical setting and a third movable entity 7 can be a fellow for the clinical setting. By way of further example, a fourth moveable entity (not shown) may be a ventilation system for a patient and a fifth moveable entity (not shown) may be a defibrillator. Thus, each moveable entity may identify a human entity (such as a particular clinician) or a non-human entity (such as a piece of medical equipment).

In other words, each moveable entity may be associated with a particular role, which role may be common to more than one moveable entity (e.g. there may be a plurality of different nurses, each having a same role of 'nurse'). A role may define a moveable entity's capabilities, job role, training level, seniority, experience and/or other defining characteristics. For non-human moveable entities, a "role" may be a use or purpose of the moveable entity (e.g. a "bed" or a "ventilation equipment"), a severity classification (e.g. a "high severity" for complex intensive care equipment or a "low" severity for vital sign monitoring equipment) and so on. It will be clear that there are at least two different possible types of role.

The location of each movable entity 5, 6, 7 is tracked, for example, using a known real-time locating system (RTLS) 8.

A real-time locating system 8 may be adapted to track when each individual moveable entity 5, 6, 7 enters or leaves a predetermined zone 11-14 of the predetermined area 1. For example, the real-time locating system 8 may be formed of network of tag/fob monitoring devices, each located at a passable boundary (e.g. a door) between different predetermined zones. An example of a suitable tag monitoring device is an access control tag reader (which allows or denies entry to a moveable entity via their tag). The real-time locating system may be adapted to give timing information indicating when a moveable object has entered/left a zone.

Other methods of tracking a location of a moveable entity are known to the skilled person (e.g. monitoring where a moveable entity is checked in and out of a zone). Other real-time locating systems are also envisaged, such as those that can track a location of an entity using a wireless signal, even if they are not explicitly tagged (e.g. tracking mobile phones), or track a location (and optionally role) of an entity using a closed-circuit television and image recognition software. Such systems are still able to report a location of an entity (resolution can vary) at regular intervals.

The real-time locating system (RTLS) 8 generates a stream of real-time location information, that can be used to identify the current location of each movable entities 5, 6, 7 within the predetermined area 1. In particular, the stream of real-time location information may be able to identify when (i.e. a time at which) a moveable entities leaves/enters a predetermined zone and which of the plurality of predetermined zones that moveable entity 5, 6, 7 is leaving/entering.

The stream of real-time location information may also be able to indicate a type/role of each moveable entity 5, 6, 7 leaving/entering a predetermined zone. This can be controlled, for example, by issuing different types of movable entity with tags having different identities—or by assigning each moveable entity a tag having a unique identity and cross-referencing a role with each unique identity (e.g. using a database).

Table 1 illustrates an extract of a typical raw RTLS stream. The TIMESTAMP indicates a point in time at which a moveable entity has indicated their location (e.g. exited and/or entered a zone), a TAG ID identifies the movable entity 5, 6, 7, and a MONITOR ID identifies the tag monitoring device 8 detecting the moveable entity. This can be used to detect a location of the entity. For example, if a monitor installed in room A (i.e. MONITOR ID="ROOM A") received a signal from tag X (i.e. TAG ID="X"), then it indicates that the entity associated with "TAG ID=X" at the relevant timestamp (TIMESTAMP) is in room A.

TABLE 1

| TIMESTAMP | TAG ID | MONITOR ID | BUTTON PRESS | TAG TYPE |
|---|---|---|---|---|
| 1493611208 | 591100 | 211190 | \|F\|F\|F\|F\|T\|F\| | 1 |
| 1493611220 | 591100 | 211190 | \|F\|F\|F\|F\|T\|F\| | 1 |
| 1493611232 | 591100 | 211190 | \|F\|F\|F\|F\|T\|F\| | 1 |
| 1493611235 | 451131 | 211190 | \|F\|F\|F\|F\|T\|F\| | 1 |
| 1493611241 | 451119 | 211190 | \|F\|F\|F\|F\|F\|F\| | 1 |
| 1493611244 | 591100 | 211190 | \|F\|F\|F\|F\|T\|F\| | 1 |
| 1493611247 | 451131 | 211190 | \|F\|F\|F\|F\|T\|F\| | 1 |

BUTTON PRESS indicates which of a plurality of buttons (here: six buttons) is pressed at the time of capturing the movement of the subject. Typically, when a button is pressed, the corresponding button will be T. In an example in which there are 6 buttons and button 5 is pressed, then this field will be FFFFTF.

TAG TYPE indicates the type of the tag, e.g. whether it is a tag to track patients (disposable wristband), to track staff (badge shaped) or to track another entity (sticker shaped). This can help identify a type of entity that is being monitored. In other words, different types of tags can be distributed to different types of entity, in order to allow different entities types to be tracked.

The stream of real-time location information can therefore indicate when a moveable entity 5, 6, 7 has changed location or has moved to a different predetermined zone 11-14.

However, typical streams of real-time location information provided by an RTLS are unstructured, and cannot be reliably processed by a machine-learning model to identify causes of occupancy (which here refers to the occurrence of a predetermined event within the predetermined area).

Hereafter described methods provide structure to the real-time location information to thereby enable processing of the real-time location information by a (first) machine-learning model to accurately determine an occupancy cause.

Figure 2:
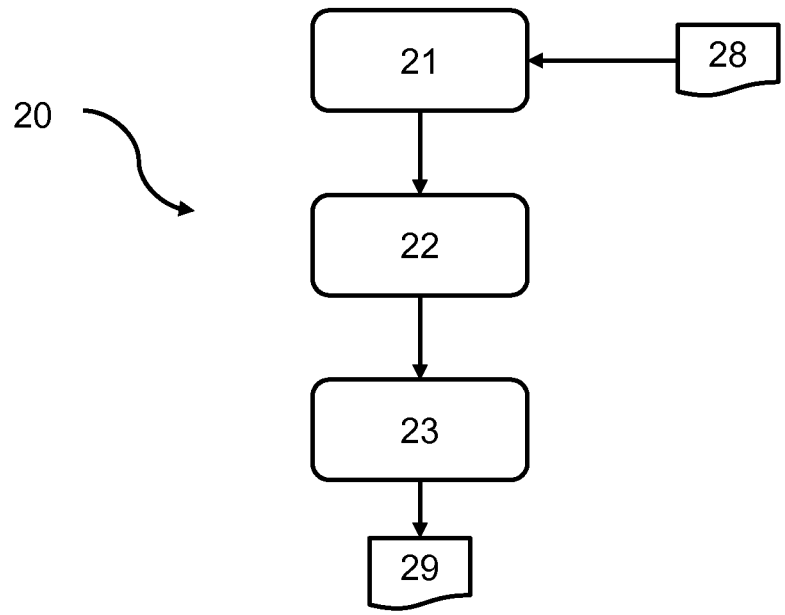
FIG. 2 illustrates a method of monitoring moveable entities within a predetermined area according to an embodiment.

FIG. 2 illustrates a method 20 of monitoring the movable entities 5, 6, 7 within the predetermined location 1.

The method 20 begins with a step 21 of obtaining the stream 28 of real-time location information identifying current locations of moveable entities within the predetermined area. Step 21 may comprise obtaining the stream 28 of real-time location information from the real-time locating system 8.

Subsequently, the method 20 performs a step 22 of processing the real-time location information to generate occupancy information of each of a plurality of predetermined zones 11-14 of the predetermined area 1.

Step 22 may, for example, comprise generating an occupancy data entry containing occupancy information for each of the plurality of predetermined zones. An occupancy data entry may indicate a current occupancy status of each of the predetermined zones, the current occupancy status being provided by the occupancy information.

In a first example, step 22 comprises identifying a number of movable entities 5, 6, 7 within each predetermined zone 11-14 at a particular point in time or an average number of movable entities 5, 6, 7 within each predetermined zone 11-14 over a period of time. Thus, occupancy information of each predetermined zone may comprise a single value indicating a number of moveable entities within the predetermined zone, so that an occupancy data entry comprises a respective value for each predetermined zone.

This may comprise, for example, processing the stream of real-time information to monitor a movement of each moveable entity between different zones to thereby identify, for a particular point in time, a current location of each movable entity. By way of example, a movement of a moveable entity from a first zone to a second zone is indicative that the moveable entity is located in the second zone. In this way, occupied zones can be identified, and the number of moveable entities within occupied zones can be identified. The number of movable entities in each predetermined zone can then be summed and output as occupancy information for each predetermined zone.

In a second example, step 22 comprises determining what types/roles of each moveable entity 5, 6, 7 are present in each predetermined zone 11-14 at a particular point in time. This may again comprise processing the stream of real-time information to monitor a movement of each moveable entity between different zones, and to monitor which roles are present in each predetermined zone (e.g. via monitoring identities of the moveable entities). In this way, the roles of entities in each predetermined zone may be identified (e.g. via identities of the moveable entities).

Thus, there may be a step (not shown) of determining one or more roles of each at least one movable entity. This may be performed, for example, by monitoring identities (e.g. TAG ID) of moveable entities within the predetermined area and cross-referencing said identities to appropriate roles. In another example, a role of a moveable entity may be ascertained from the tag type (e.g. if different tag types are distributed to different types/roles of moveable entities). In some examples, both the identity of the moveable entity and the tag type may be processed (e.g. cross-referenced to a database) in order to establish the role/type of the entity.

In this way, an occupancy data entry may comprise information on the role(s) of moveable entities in each predetermined zone.

In a third, preferred, example, step 22 comprises identifying a number of moveable entities 5, 6, 7 associated with each of a plurality of different roles/types, in each predetermined zone 11-14.

Thus, as illustrated in Table 1 below, step 22 may comprise generating an occupancy data entry indicating (for a particular instant or point in time), in each predetermined zone 11-14 (Table 1: "Zone"), a number (Table 1: "Number") of movable entities 5, 6, 7 of each of a predetermined number of types/roles (Table 1: "Entity Type").

TABLE 1

| Zone | 11 | | | 12 | | | 13 | | | 14 | | |
|---|---|---|---|---|---|---|---|---|---|---|---|---|
| Entity Type | 5 | 6 | 7 | 5 | 6 | 7 | 5 | 6 | 7 | 5 | 6 | 7 |
| Number | 1 | 0 | 0 | 2 | 1 | 0 | 0 | 0 | 1 | 0 | 1 | 0 |

In particular, Table 1 indicates a number of nurses 5, physicians 6 and fellows 7 in each room 11-14 of the predetermined area 1. Thus, there is a single nurse 5 in the first predetermined zone 11 (ward), two nurses 5 and a physician 6 in the second predetermined zone 12 (examination room), one fellow 7 in the third predetermined zone 13 (control room) and one physician 6 in the fourth predetermined zone 14 (corridor).

Thus, the occupancy information obtained in step 22 preferably indicates at least a number of moveable entities in each predetermined zone 11-14 at a particular point in time. Even more preferably, the occupancy information indicates a number of moveable entities of each known role in each predetermined zone 11-14.

Thus, there may be a step (not shown) of determining one or more roles of each at least one movable entity. This information may be used to determine how many entities of each role are present in each predetermined zone.

Thus, occupancy information may indicate, for a particular zone at a particular point in time, a number of each type/role of moveable entity within that zone. However, other occupancy information can be obtained, for example, indicating a frequency at which (or number of times that) different type/roles of moveable entities move in and out of the predetermined zone during a period of time immediately preceding a specific point in time.

Thus, step 22 comprises processing the stream of real-time location information in order to place the information contained therein in a structured format that can be processed by a machine-learning model. In particular examples, counts of how many moveable entities in each predetermined zone, and preferably counts of how many moveable entities of each type in each predetermined zone, are determined.

In particular, step 22 may comprise generating at least one occupancy data entry providing a snapshot of occupancy information for each predetermined zone (i.e. at a particular point in time).

After processing the stream of real-time location, RTL, information in step 22, the processed portions of the stream may be discarded (i.e. no longer stored or deleted). This helps improve a privacy of the moveable entities, as the occupancy information can be anonymized (unlike the stream of RTL information).

Following step 22, the method 20 performs step 23 of processing the occupancy information using a (first) machine-learning model to identify at least one occupancy cause 29 of the plurality of predetermined zones.

The (first) machine-learning model is adapted to map the occupancy information to a cause of occupancy. In particular, the machine-learning model may define a relationship between occupancy information and (at least one) occupancy cause.

The (first) machine-learning model may be adapted to process the occupancy information of each zone as a whole (i.e. rather than processing each occupancy information individually) in order to determine an occupancy cause.

As an explanative example, the presence of all known moveable entities within a single predetermined zone—so that no other zones are occupied—may be indicative of a team meeting (i.e. the occupancy cause is that a team meeting has occurred). In another example, the presence of all physicians and fellows within a ward may indicate a traumatic event in the ward (e.g. a patient undergoing cardiac arrest), which might be the only reason that all said moveable entities would have reason to occupy the ward—i.e. is an occupancy cause.

In particular, step 23 of method 1 may comprise processing the occupancy information of each predetermined zone using a (first) machine-learning model to identify whether, or a probability that, a predetermined event has influenced the occupancy information. In other words, step 23 may comprise determining whether a predetermined event has occurred based on the occupancy information of each zone of the predetermined area.

In this way, a (first) machine-learning model may be adapted to identify whether a particular predetermined event occurs in the predetermined area 1, or to predict a probability that a particular predetermined event has occurred.

Thus, the machine-learning model may be adapted to map or relate occupancy information to events (such as a surgery or team meeting). In this way, events occurring in the predetermined area can be identified.

Step 23 may comprise processing the occupancy information with a plurality of different machine-learning models, each adapted to determine whether a particular predetermined event occurs in the predetermined area or a probability that a predetermined event has occurred.

Thus, step 23 may comprise checking whether any of a plurality of predetermined events have influenced or are associated with the occupancy data entry (comprising occupancy information of each predetermined zone), using a respective plurality of machine-learning models.

Although it is possible to derive, using a machine-learning model, an occupancy cause using a data entry representative of a single point/moment in time (as described above), for improved prediction power of the machine-learning model, a dynamic view of the occupancy information (i.e. over a period of time) can be used.

Thus, in a preferred embodiment, step 22 comprises obtaining a plurality of sequential occupancy data entries (i.e. a sequence of occupancy data entries), where each data entry is associated with a different point/moment in time. Later data entries in the sequence are associated with a later point in time than earlier entries in the sequence. It will be clear that each sequence of occupancy data entries is therefore associated with a defined period of time—being the period of time spanning from a point in time associated with a first data entry to a point in time associated with the last/final data entry in the sequence.

Accordingly, step 23 may comprise processing the sequence of occupancy data entries using the machine-learning model to determine or predict an occupancy cause of one or more predetermined zones of the predetermined area.

In particular, step 23 may comprise determining, using the machine-learning model, whether a predetermined event has influenced the sequence of occupancy data entries For example, step 23 may comprise using the machine-learning model to determine whether one or more predetermined events occurs during a time window associated with or covered by the sequence.

Of course, more than one machine-learning model may be applied, each machine-learning model being adapted to identify whether a different predetermined event has occurred.

Examples of predetermined events (where a predetermined area is in a clinical setting) include: performance of a first or second type of surgery; a team meeting; a patient examination process; a patient check-up process; patient registration; a consultation process; a transportation process; a patient preparation process (e.g. in a holding area); a surgical room preparation process (e.g. disinfection process) and so on.

It has been recognized that changes in the location(s) of at least one moveable entity can be indicative of a cause of occupation of the predetermined zone(s). This improves an accuracy of the step of determining an occupancy cause.

By way of example, in a scenario in which a physician moves from a pre-surgical cleaning facility to a surgery, such a scenario may be indicative that a surgery will take place (i.e. a surgery is the cause of occupancy of the surgery). Other examples will be apparent to the skilled person.

Each data entry of the sequence of occupancy data entries represents a different time sample of occupancy information of each of the plurality of predetermined zones. Thus, each occupancy data entry in the sequence represents a different point in time and reflects an overall occupancy status of the predetermined area at a point in time.

Table 2 illustrates an example of a sequence of occupancy data entries formed of six different occupancy data entries (labelled by number in the sequence—Seq. No.). Each data entry indicates how many of each of a plurality of different types (Entity Type) of movable entity 5, 6, 7 are in each predetermined zone 11-14 (Zone) at a given moment in time. It can be clearly seen in Table 2 how the location of moveable entities can change over time, i.e. as moveable entities move about the predetermined area and into different zones.

TABLE 2

| Zone | 11 | | | 12 | | | 13 | | | 14 | | |
|---|---|---|---|---|---|---|---|---|---|---|---|---|
| Entity Type | 5 | 6 | 7 | 5 | 6 | 7 | 5 | 6 | 7 | 5 | 6 | 7 |
| Seq. No | | | | | | | | | | | | |
| 1 | 1 | 0 | 0 | 2 | 1 | 0 | 0 | 0 | 1 | 0 | 1 | 0 |
| 2 | 1 | 0 | 0 | 2 | 0 | 0 | 0 | 1 | 1 | 0 | 1 | 0 |
| 3 | 0 | 0 | 0 | 2 | 1 | 0 | 0 | 1 | 1 | 1 | 0 | 0 |
| 4 | 0 | 0 | 0 | 2 | 1 | 0 | 0 | 1 | 1 | 1 | 0 | 0 |
| 5 | 0 | 0 | 0 | 3 | 2 | 0 | 0 | 0 | 1 | 0 | 0 | 0 |
| 6 | 0 | 0 | 0 | 3 | 2 | 0 | 0 | 0 | 1 | 0 | 0 | 0 |

The sequence generated in step 22 can be processed by a machine-learning model in step 23 to identify an occupancy cause of at least one zone of the predetermined area.

In particular, step 23 may comprise processing the sequence of occupancy data entries with one or more machine-learning models to identify whether one or more predetermined events have occurred (in the predetermined area).

For example, each of a plurality of machine-learning models may be tuned to determine whether a particular predetermined event has occurred or a probability that a particular predetermined even has occurred, where each machine-learning model is adapted to identify a different event.

Even more preferably, step 22 may comprise generating a plurality of sequences of occupancy data entries. Each of the plurality of sequences may be temporally offset from one another—i.e. form a sequence/series of sequences. Each sequence in the sequence of sequences may be associated with a period of time later than a period of time associated with an earlier sequence in the sequence of sequences.

In other words, a step of generating the sequence of occupancy data entries can be iteratively performed, to generate a plurality of sequences of occupancy data entries. Preferably, the plurality of sequences forms a series of sequences arranged in an order in which they are generated.

Figure 3:
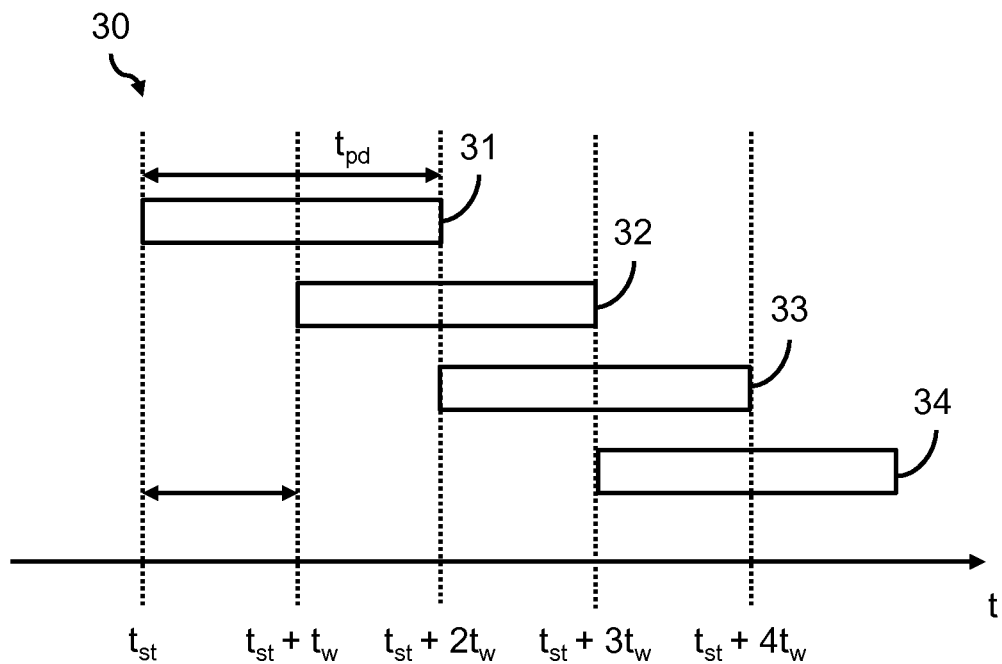
FIG. 3 illustrates sequences of occupancy data entries for processing by a machine learning model to determine an occupancy cause.

FIG. 3 illustrates a series 30 of sequences 31-34 that may be generated in step 22 of method 20.

Each sequence 31-34 is associated with a period of time having a predetermined length $t_{pd}$. Each consecutive sequence 31-34 is associated with a period of time or time window beginning at a later point in time than an earlier sequence in the series.

Put another way, a first sequence 31 may cover a period of time having a predetermined length $t_{pd}$ beginning at a specific start time $t_{st}$. The second sequence 32 in the series covers a period of time (of the predetermined length $t_{pd}$) beginning a time interval $t_w$ after the specific start time $t_{st}$ (i.e. at $t_{st}+t_w$). Each following sequence begins an additional time interval $t_w$ after the preceding sequence.

Each sequence in the series itself comprise a sequence of occupancy data entries. As previously explained, each occupancy data entry can indicate occupancy information for each of a plurality of predetermined zones at a particular point or moment in time. Thus, each occupancy data entry can represent a sample of occupancy information for the predetermined area.

To form the series 30 of sequences, a sampling process may take place. At a specified start time $t_{st}$, a predetermined number s of samples of occupancy information may be taken every $t_i$ seconds to form a sequence (comprising s occupancy data entries and associated with a period of time having length $s.t_i$). Then, beginning at a time interval $t_w$ after the specified start time $t_{st}$, the process may begin again. The process may be iteratively repeated to obtain the series of sequences.

Thus, sequences can overlap with one another, so that a plurality of sequences share one or more (but preferably not all) data occupancy entries.

Each of the sequences of occupancy data entries in the series may be individually processed by the machine-learning model to identify an occupancy cause during each time period covered by a respective sequence of occupancy data entries.

The processing by the machine-learning model may be performed once a sequence of occupancy data entries is available (i.e. all occupancy data entries for a sequence have been captured). This allows for a live or continuous detection of occupancy causes, such as detection of an ongoing predetermined event.

By overlapping the sequences (such as illustrated in FIG. 3), an improvement to a continual real-time detection of occupancy causes can be realized. By way of example only, a sequence may represent a period of time lasting tens of minutes. Thus, if there is no overlap then predictions can only be given every tens of minutes. However overlapping is allowed (e.g. a new sequence begins every minute) then predictions can be made more frequently (e.g. every minute). This would allow us to give more frequent predictions to support real-time use cases.

It has previously been described how (one or more) machine-learning models may process a sequence of occupancy data entries in order to identify whether a predetermined event has occurred, where the predetermined event forms the occupancy cause. In particular, the machine-learning model may be adapted to identify the influence of a predetermined event on a sequence of occupancy data entries.

Machine-learning models are well known in the prior art, and typically operate by applying a series of algorithmic steps, layers or masks to input data in order to predict output data. Typically, the output data indicates an answer to a predetermined question that the machine-learning model is intended to answer (e.g. "has a particular predetermined event taken place?"). Examples of machine-learning models include neural network models and deep learning models.

Thus, a machine-learning model is any structure or process that enables the prediction of (values for) certain output data based on input data—e.g. calculating a probability that a predetermined event has occurred based on an input sequence of occupancy data entries.

Typically, to train a machine-learning model, training data is collected that associates known examples of input data (e.g. a sequence of occupancy data entries) with known examples of output data (e.g. whether a particular predetermined event has occurred). A (generic) machine-learning model is then applied to each example of input data in an attempt to predict respective examples of output data. The predicted examples of output data are then compared to the known examples of output data, e.g. an error measure between the predicted and known examples is determined. Based on the comparison, the machine-learning model is refined with the aim of improving the performance of the machine-learning model (i.e. improving an accuracy of the prediction). This process may be repeated iteratively to thereby train or tune the model to perform a specific task (e.g. identify occurrence a predetermined event).

Methods of training, refining or otherwise 'optimizing' a machine-learning model, e.g. based on error measures between predicted and known examples of output data, will be well known to the person skilled in the art.

An embodiment of generating training data is described below, where the training data can be used to generate a machine-learning model that processes a sequence of occupancy data entries to predict whether a single predetermined event has occurred or a probability that the single predetermined event has occurred. The skilled person would be able to adapt the below described approach for other examples of occupancy information.

However, training data that identifies known examples of sequences (and whether they are associated with a known predetermined event) may not be readily available. Thus, it may be necessary to generate suitable training data formed of suitable examples of sequences and their association or non-association with a predetermined event.

Thus, entries for training data may indicate whether a given sequence corresponds to a given event.

In particular, each entry of the generated training data comprises a historic sequence S (i.e. an example of a sequence that has occurred in the past) and an event label $L_e$, which indicates whether the historic sequence S and a predetermined event E correspond to one another (i.e. whether a historic sequence S is indicative of the predetermined event E). By way of example, an event label $L_e$ '0' can indicate that the predetermined event E is not ongoing when a historic sequence S occurs (i.e. they do not correspond to one another), and an event label $L_e$ '1' can indicate that a predetermined event E is ongoing when a historic sequence S occurs (i.e. they correspond to one another). Of course, these labels may be reversed.

The skilled person will appreciate that different blocks/sets of training data may be generated for different predetermined events. Each block/set of training data may be individually used to train a different machine-learning model to identify or predict the probability that a particular predetermined event (associated with the block/set of training data) is associated with a sequence of occupancy data entries.

To generate the training data, a plurality of historic sequences and instances of the predetermined event should be obtained, where each historic sequence and occurrence of a predetermined event has a defined start and end time. Such data can be obtained, for example, by recording sequences of occupancy data and manually monitoring (e.g. in person or using CCTV) the start and finish of events as the sequences of occupancy data are recorded.

If a historic sequence entirely overlaps a time over which an instance of the predetermined event occurs, an entry for the training data can be generated that indicates that the two are associated (e.g. having event label $L_e$ '1'). Similarly, if there is no overlap a historic sequence and a time over which any instance of the predetermined event occurs, an entry for the training data can be generated that indicated that the two are not associated with one another (e.g. having event label $L_e$ '0').

In some embodiments, if there is a partial overlap between a historic sequence and an instance of the predetermined event, no training data is generated (i.e. the information is discarded). This is to avoid inaccurately associating historic sequences with a predetermined event, thereby improving a reliability of the training data.

Such training data can be used to train or refine a machine-learning model, according to well-known machine-learning model training principles.

To provide additional entries for the training data, it can be determined that a historic sequence is associated with the predetermined event if the sequence of occupancy data overlaps an instance of the predetermined event for at least a predetermined period of time $t_{ev}$. In some embodiments, if a historic sequence partially overlaps an instance of the event (but does not exceed the predetermined period of time), no data entry is generated for the training data.

Thus, an event label $L_e$ can be calculated for each sequence S, for a particular predetermined event, using the following relationship (where E represents an instance of a predetermined event):

$$L_e = \begin{cases} 1 & \text{if Overlap } (S, E) \geq t_{ev} \\ \text{Discard} & \text{if } 0 < \text{Overlap } (S, E) < t_{ev} \\ 0 & \text{if Overlap } (S, E) = 0 \end{cases}$$

Thus, training data can be generated by determining whether there is an overlap between instances of a predetermined event and historic sequences, and whether a length of the overlap exceeds a predetermined period of time $t_{ev}$.

Figure 4:
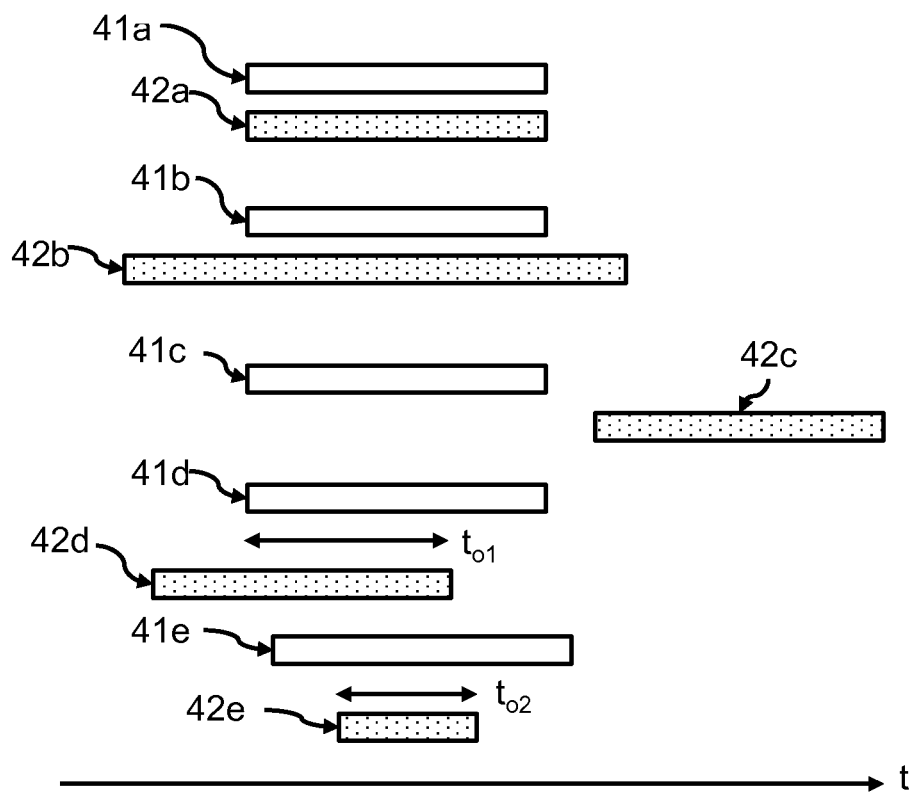
FIG. 4 illustrates how to associate historic sequences with a predetermined event.

Explanative examples of historic sequences and instances of a predetermined event are provided in FIG. 4. In particular, FIG. 4 illustrates different scenarios for historic sequences of occupancy data 41a-41e and instances of a predetermined event 42a-42e, which have the potential to form training data. Each historic sequence and instance of a predetermined event has a set start and end time. In other words, the length and start time of each historic sequence and each instance of the predetermined event is known.

By way of example only, each instance of the predetermined event may represent a different instance of a particular surgical procedure (i.e. each instance may represent a different surgery).

A first sequence 41a can be associated with the predetermined event as the first sequence 41a begins and ends at an approximately same point in time as a first instance 42a of the predetermined event. Thus, an entry for training data (for the predetermined event) can be generating comprising the first historic sequence and an event label $L_e$ '1'.

Similarly, a second sequence 41b can be associated with the predetermined event—as the second sequence 41b entirely overlaps a second instance 42b of the predetermined event (i.e. an instance of the predetermined event is ongoing as the second sequence occurs). Thus, the second sequence and predetermined event can be associated with one another. Thus, an entry for training data (for the predetermined event) can be generating comprising the second historic sequence 41b and an event label $L_e$ '1'.

However, a third sequence 41c cannot be associated with the predetermined event, as there is no overlap between the third sequence and a third instance 42c of the predetermined event. Thus, an entry for training data (for the predetermined event) can be generating comprising the third historic sequence 41c and an event label $L_e$ '0'

A fourth sequence 41d and a fourth instance 42d of the predetermined event 42d partially overlap one another. The length of time $t_{o1}$ for which they partially overlap one another is greater than a predetermined length of time $t_{ev}$. Thus, the fourth sequence and the predetermined event can be associated with one another. Thus, an entry for training data (for the predetermined event) can be generating comprising the fourth historic sequence 41d and an event label $L_e$ '1'.

A fifth sequence 41e and fifth instance 42e of the predetermined event also partially overlap one another; however, the period of overlap $t_{o2}$ is not greater than a predetermined length of time $t_{ev}$. Thus, it cannot be assumed that the fifth sequence 41e and the predetermined event correspond to one another. However, it cannot be confirmed that there is no correspondence between the fifth sequence 41e and the predetermined event (as the overlap is greater than 0). Thus, for the sake of ensuring accurate training data, no data entry for the training data is generated in this scenario.

In this way, training data is generated that associates historic sequences of occupancy data entries with a predetermined event. This training data can be used to train the machine-learning model.

In one example of a training process, N sets of training data can be generated using the above process (for different predetermined events), in order to train N machine-learning models, each machine-learning model being associated with a different predetermined event. Thus, N machine-learning models may be individually trained for each of N predetermined events.

In one example, each data entry of training data for training a machine-learning model comprises a historic sequence of occupancy data entries and an event label '1' or '0'. As described above, each historic sequence of occupancy data entries may comprise, for example, a matrix having f columns and l rows. Each row represents a different instance of an occupancy data entry (i.e. a different sample of occupancy information). The columns can be formed of X sets of Y columns (each set containing occupancy information, and each set being associated with a predetermined zone—i.e. X indicates a number of predetermined zones), where each column of a set of indicates a number of moveable entities of a particular role in the predetermined zone (i.e. Y indicates a number of different roles of moveable entities). Thus, the number of columns in the matrix is equal the product of X and Y.

The event labels can thereby serve as model training targets for training a machine-learning model.

Figure 5:
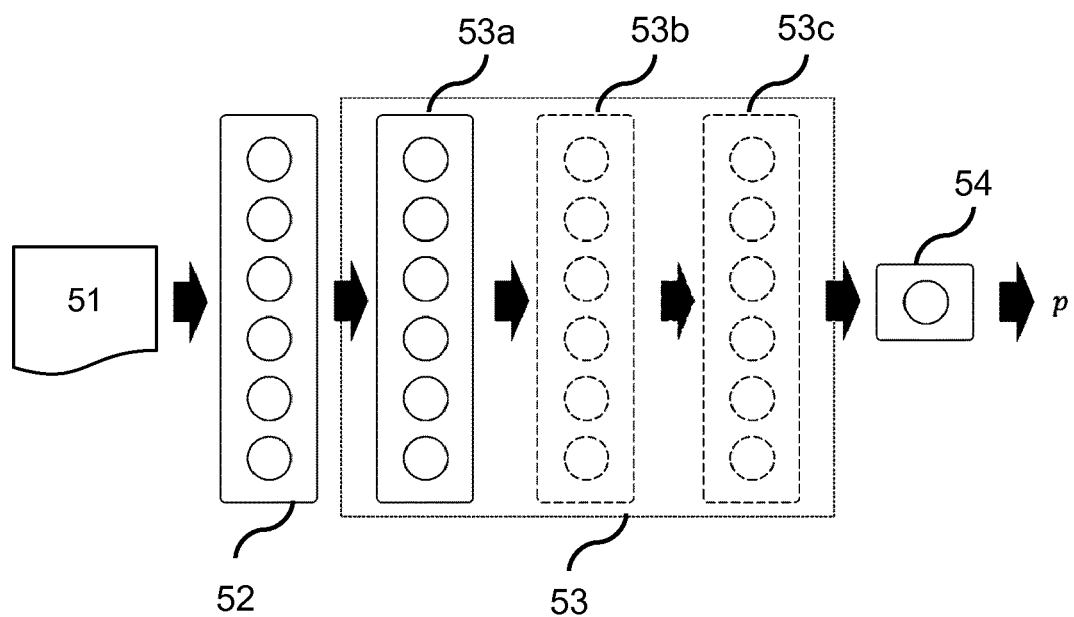
FIG. 5 illustrates a structure of a machine learning model according to an embodiment.

FIG. 5 demonstrates the structure 50 of a machine-learning model for predicting the (probability p of the) occurrence of a predetermined event based on a sequence 51 of occupancy data entries, according to an embodiment of the invention.

The structure 50 comprises a one-input layer 52 to take a sequence 51 in a matrix form (e.g. as exemplified in Table 2). The dimensions of the matrixes are fixed (i.e. the sequence of occupancy data entries is in a fixed format). The input layer will feed a set 53 of one or more hidden layers 53a-53c, each having LSTM (long short-term memory) and dropout nodes. The output of the set of hidden layers feeds an output layer 54 with a single dense neuron. This dense neuron can produces a floating or decimal number between 0 and 1 that indicates the probability that the predetermined event is ongoing during the time window of the sequence 51 input to the machine-learning model.

To evaluate and refine a machine-learning model for identifying (the probability of) a predetermined event, it is preferred to use an evaluation framework.

An evaluation framework may comprise splitting training data for a particular predetermined event into different groups, and using the different groups of training data for different purposes.

In particular embodiments, the training data may be divided into three different groups: a training group; a validation group and a testing group.

The training group of the training data is used to train and adapt the machine-learning model for predicting (a probability of) whether a particular predetermined event has occurred in a time window covered by a sequence of occupancy data entries. Training of a machine-learning model may use any standard training methodology, such as stochastic/incremental gradient descent (SGD) or the "Adam" algorithm. The validation group is used to tune the parameters of the machine-learning model, to ensure that the machine-learning model is not biased towards the testing group only. The testing group is used to assess the accuracy or performance of the machine learning model, to evaluate whether the machine learning model has bene successfully adapted so that it can accurately predict the (probability of) whether the predetermined event has occurred in a time window covered by a sequence of occupancy data entries.

The performance of the machine-learning model can be evaluated using any known learning classification metrics such as accuracy, precision, recall, ROC (Receiver operating characteristic) curve and AUC (Area Under Curve). However, as it has been recognized that training data for the present invention is usually skewed (as there are typically more '0's in the labels than '1's), it is advisable to use metrics which are insensitive to skewness, such as AUC.

The proportion of the division of training data into the three different groups is flexible, for example 4:3:3 or 5:3:2 respectively. It has been recognized that sequences (of training data) that cover time windows that are close to one another will probably have similar event labels. Thus, adjacent sequences should not be split across different groups (as this may lead to a false assessment of machine-learning model accuracy).

For example, training data may cover a period of 10 days, of which the first 4 days may be used as the training group; the 5th, 6th and 7th days may be used as the validation group and the 8th, 9th and 10th days as the testing group.

The above described training methods have been directed towards an embodiment in which a machine learning model is trained to identify whether (or a probability that) a single predetermined event occurs during a time window covered by a sequence of occupancy data entries—each occupancy data entry comprising, for each of a plurality of zones of a predetermined area, occupancy information of that zone. In particular, the trained machine-learning model is adapted to process a sequence of occupancy data entries to identify whether or a probability that the predetermined event occurs during the time window associated with the sequence.

However, training methods may be adapted for other machine learning models, for example, to process other input data (such as a single occupancy data entry) to identify an occupancy cause, i.e. the occurrence of a predetermined event.

A predetermined event may be alternatively labelled a "collaborative event", as they typically require the presence of more than one moveable entity (i.e. the entities collaborate in order to perform the predetermined event).

Proposed methods can be employed to monitor an ongoing occupancy cause (such as whether a predetermined event is currently occurring) based on a continual processing of occupancy information.

In at least one embodiment, this continual monitoring can be exploited to generate an alert when an incorrect occupancy cause (i.e. predetermined event) is occurring. In particular, a detected cause of occupancy can be compared to a scheduled cause of occupancy, and an alert may be generated if the two do not match.

For example, if a first predetermined event (e.g. a surgery on a patient occupying a first ward) is scheduled to be currently occurring, but a machine learning model indicates that second, different predetermined event (e.g. a surgery on a patient occupying a second ward) is currently occurring, an alert may be generated to indicate that an incorrect or unscheduled predetermined event is ongoing.

Similarly, if a first predetermined event is scheduled, and it is determined that this first predetermined event is not ongoing, an alert may be generated to identify that the first predetermined event has not occurred.

In this way, proposed embodiment provide automated detection of whether moveable entities in the predetermined area are adhering to scheduled tasks or events, by processing the real-time locations of said movable entities. One or more alerts can be generated if said moveable entities are not adhering to scheduled tasks or events.

Such proposed embodiments can help prevent incorrect events from occurring (such as an incorrect operation on a patient) and reduce mistakes in performing tasks in the predetermined area.

Alerts may, for example, be in the form of a visual, audio or haptic alert, or may be an electronic alert (such as a log or flag in data).

In another example, if a first predetermined event (e.g. a first medical exam) finished earlier than expected (e.g. 10 AM instead of 11 AM), then an alert can be generated to advise that a subsequently scheduled event (e.g. a second medical exam) can be started earlier, or that the relevant room is free for an additional event (e.g. a third medical exam or a cleaning process) to take place. Such an example may result in higher room utilization (more exams can be arranged), thereby reducing patient waiting time.

In an embodiment, a display (such as a screen) could be set-up for displaying an automatically determined occupancy cause. This improves an understanding of potential customers, staff and clients without the need for said persons to request information (e.g. from potentially busy entities) as to a progress of an event.

For example, a display may be set up at the waiting area of an operation theatre. The machine learning model can determine the predetermined event occurring in the operation theatre (for example, room being prepared, patient being transported, operation ongoing, operating wrapping up etc.) automatically and display the occupancy cause on the screen so that subjects, future patients and/or hospital staff can know the progress/state of the operation without needing to enter the operation theatre or ask the physicians/ surgeons exiting the theatre.

Thus, embodiments may further comprise a display for displaying the occupancy cause for viewing by subjects and/or other persons.

In further examples, the determined cause of occupancy may be passed to a hospital's (or other predetermined area) reporting system. In this way, managers can have automated reports of statistics of room utility, e.g. distribution of when different exam times occur, without needing to hire persons to observe this data as this data can be collected automatically. Thus, an efficiency of usage of the predetermined area can be increased.

In addition to identifying the occurrence of a predetermined event within one or more predetermined zones (i.e. identifying occupancy causes), some methods may also comprise a further step of estimating/determining a remaining time for, or a progress of, a (ongoing) predetermined event.

In a simple embodiment, this may be performed by: identifying a start time of an ongoing predetermined event, which may be based upon a time at which a previously described machine-learning method recognizes the occurrence of the ongoing predetermined event; determining an amount of time elapsed since the start time (e.g. a difference between a current time and the start time); and determining a difference between the amount of time elapsed and a predicted length of time for performing the ongoing predetermined event.

The predicted length of time for performing an ongoing predetermined event may be calculated from predetermined values for the length of a predetermined event, e.g. set out in a look-up table. By way of example, each possible predetermined event may be associated with a respective predicted length of time, e.g. based upon historical averages/ trends or clinical guidelines/recommendations.

In a more complex embodiment, estimating/determining a remaining time for a (ongoing) predetermined event may comprise determining a current sub-stage of the predetermined event by processing the occupancy information. In particular, each predetermined event may be divided into a plurality of different sub-stages, which can be identified using a machine-learning method. Once the current sub-stage, of the ongoing predetermined event, is identified, it is possible to predict a length of time remaining to complete the predetermined event (e.g. to complete the remaining substages), which may again be based upon historical averages/trends and/or clinical guidelines/recommendations.

In some embodiments, a second machine-learning method is used to estimate/determine a remaining time for an ongoing predetermined event. This may be performed in a conceptually similar manner to the previously described machine-learning method.

There may be a respective second machine-learning method for each predetermined event, and the appropriate second machine-learning method may be selected for estimating the remaining time for the corresponding ongoing predetermined event.

In one example, a second machine learning method may receive, as input, an identify of a predetermined event detected by the earlier machine learning method and an elapsed time of the predetermined event, and output a prediction of the remaining time of the detected predetermined event.

In examples, a first machine-learning method may process occupancy information of each of a plurality of predetermined zones to detect the occurrence of a predetermined event and a second machine-learning method may process the same occupancy information to determine a remaining time for the detected predetermined event.

The occupancy information may include a sequence of occupancy data entries, each occupancy data entry providing occupancy information of each of a plurality of predetermined zones (as previously described).

In some embodiments, the second machine-learning method may use an elapsed time of the predetermined event as an additional input, i.e. alongside the occupancy information, for determining the remaining time for the predetermined event.

One example uses an extended version of the previously described occupancy data entries to provide data suitable for predicting a remaining time for an ongoing predetermined event. In particular, one method comprises identifying a start time of an ongoing predetermined event (e.g. a time at which an ongoing predetermined event is identified); determining a time elapsed since the start time for each occupancy data entry and providing each occupancy data entry with a time elapsed since a start time of the associated predetermined event. The time elapsed may be calculated, for example, by determining a start timestamp at which the current event starts and calculating an elapsed time using the start time stamp and the timestamp of the occupancy data entry. The occupancy data entry/entries can then be processed using a machine-learning method to predict how long remains for the predetermined event.

It will be clear that each occupancy data entry can be associated with a particular identified event (i.e. the event determined to occur during that occupancy data entry).

It has previously been described how a predetermined event can be detected by processing a sequence of occupancy data entries using a machine-learning method. This sequence of occupancy data entries can be modified to provide a suitable input for a machine-learning method for predicting a remaining time for completing the predetermined event.

In some embodiments, a sequence of occupancy data entries may be formed, each occupancy data entry in the sequence also including a data field indicating a length of time elapsed since the event (corresponding to the occupancy data field) begun (or was first detected). This forms a "modified sequence of occupancy data entries".

The step of determining remaining time for an ongoing predetermined event may comprise processing the modified sequence of occupancy data entries using the second machine-learning method to determine how long remains for the predetermined event.

Table 3 illustrates an example of a modified sequence of occupancy data entries, which is identical to Table 2 (used to predict the occurrence of a predetermined event—i.e. a predetermined event associated with the sequence of occupancy data entries) with an additional data field for each occupancy data entry indicating a time elapsed since the beginning of the predetermined event (or since it was detected that the predetermined event was occurring).

TABLE 3

| Zone | 11 | | | 12 | | | 13 | | | 14 | | | Time |
|---|---|---|---|---|---|---|---|---|---|---|---|---|---|
| Entity Type | 5 | 6 | 7 | 5 | 6 | 7 | 5 | 6 | 7 | 5 | 6 | 7 | Elapsed (s) |
| Seq. No | | | | | | | | | | | | | |
| 1 | 1 | 0 | 0 | 2 | 1 | 0 | 0 | 0 | 1 | 0 | 1 | 0 | 115 |
| 2 | 1 | 0 | 0 | 2 | 0 | 0 | 0 | 1 | 1 | 0 | 1 | 0 | 120 |
| 3 | 0 | 0 | 0 | 2 | 1 | 0 | 0 | 1 | 1 | 1 | 0 | 0 | 125 |
| 4 | 0 | 0 | 0 | 2 | 1 | 0 | 0 | 1 | 1 | 1 | 0 | 0 | 130 |
| 5 | 0 | 0 | 0 | 3 | 2 | 0 | 0 | 0 | 1 | 0 | 0 | 0 | 135 |
| 6 | 0 | 0 | 0 | 3 | 2 | 0 | 0 | 0 | 1 | 0 | 0 | 0 | 140 |

The inventors have recognised that the progress of a predetermined event influences the movement of moveable entities within the predetermined zones. Thus, a remaining time of an ongoing predetermined event can be more accurately predicting by monitoring the movement of the moveable entities (e.g. using the sequence of occupancy data entries).

Purely by way of example, it may be known that, for a certain part of a predetermined surgical procedure, two surgeons are required (rather than one). Thus, the entry of a second surgeon into a particular zone may indicate that the certain part of the predetermined surgical procedure has commenced, thereby indicating a current progress of the surgical procedure (which influences the remaining time of the surgical procedure).

The calculated remaining time may be presented, e.g. via a user interface.

A brief explanation of machine-learning methods has previously been provided. The second-machine learning method employs similar principles.

An embodiment of generating training data for the second machine-learning method is described below, where the training data can be used to generate the second machine-learning model that processes a modified sequence of occupancy data entries to predict a remaining time for a predetermined event. The skilled person would be able to adapt the below described approach for machine-learning methods adapted to predict a progress of a predetermined event.

The desired training data for the second machine-learning model would provide, as input examples, a modified sequence of occupancy data entries (each data entry providing relevant occupancy information and an elapsed time) and, as output examples, a remaining time for the predetermined event (associated with the modified sequence).

Typically, available information for preparing suitable training data would comprise example sequences of occupancy data entries and known occurrences of predetermined events (and the start and end times of both). Typically, the predetermined events are manually labelled.

As previously explained, this available information may be obtained by obtaining a plurality of historic sequences and instances of the predetermined event should be obtained, where each historic sequence and occurrence of a predetermined event has a defined start and end time. Such data can be obtained, for example, by recording sequences of occupancy data and manually monitoring (e.g. in person or using CCTV) the start and finish of events as the sequences of occupancy data are recorded. This has been previously illustrated in FIG. 4.

To generate the training data for the second machine-learning method, then appropriate instances for the input examples of the training data should be selected. In other words, only some of the sequences of occupancy data entries may provide suitable training examples for calculating a remaining time of a predetermined event, e.g. by being sufficiently associated with or indicative of the occurrence of a predetermined event.

Initially, if the sequence of occupancy data entry does not overlap with a predetermined event, then the sequence can be discarded. This would mean that only those sequences that have a relation to a predetermined event in time are selected for forming the training data.

In a second step, if the sequence of occupancy data entry has an end time at or before the end time of the overlapping predetermined event, then that sequence can be selected as an input example. This provides input examples from which there is some remaining time before the end of the associated predetermined event.

In some embodiments, to provide further input examples a threshold t could be set, and the sequences meeting a certain criterion (e.g. a difference between the end time of the sequence $t_{end(s)}$ and the end time of an overlapping (later finishing) predetermined event $t_{end(e)}$ is equal or greater than t) can also be selected as an input example.

Having established suitable input examples for the training data, it is necessary to generate a corresponding output example for each input example. This may be performed by simply determining the difference between the end time of the predetermined event overlapping the sequence (forming the input example) and the end time of the sequence. In a further embodiment, the following relationship can be used:

$$\text{remaining time}_i = \begin{cases} T_{end}(e) - T_{end}(s), & \text{if } T_{end}(e) - T_{end}(s) \geq 0 \\ 0, & \text{otherwise} \end{cases}$$

This provides a suitable example output for each (selected) example input, thereby generating the training data for the second machine-learning method.

In some embodiments, a plurality of second machine-learning methods are generated, one for each type of predetermined event. The skilled person would be readily capable of generating suitable training data for each of a plurality of predetermined events (e.g. by restricting the selection of sequences to those that overlap the corresponding predetermined event).

Methods of training a machine-learning algorithm have been previously described, and could be adapted for training the second machine-learning method (using the appropriate training data).

Whilst previous embodiments have been described in the context of predicting a remaining time for a predetermined event, embodiment also extend to method of predicting a progress (e.g. a percentage progress) of the predetermined event. Thus, reference to the term "remaining time" may be replaced by the term "progress", mutatis mutandis.

Of course, it will be appreciated that it is not essential that the herein described methods of identifying the occurrence of a predetermined event are used. Rather, any method of identifying the occurrence of a predetermined event from occupancy information could be utilized, and subsequently processed to identify a remaining time of the detected predetermined event, e.g. in accordance with described examples.

Whilst above embodiments have been described in the context of moveable entities being health-care professionals, it will be appreciated that embodiments may extend to monitoring other persons—such as patients or visitors—as well as monitoring inanimate moveable objects—such as beds, medical equipment and so on. Thus, a moveable entity may be any animate or inanimate moveable entity/asset within the predetermined zone.

It will also be appreciated, as described previously in brief, that the predetermined area need not be in a clinical setting. For example, a predetermined area may be an industrial location (such as a factory), with different zones representing different areas of the industrial location. A possible occupancy cause (predetermined event) of a factory could indicate, for example, a particular stage of a manufacturing procedure (e.g. a coating, cutting or stamping stage). Other examples will be readily apparent to the skilled person.

Figure 6:
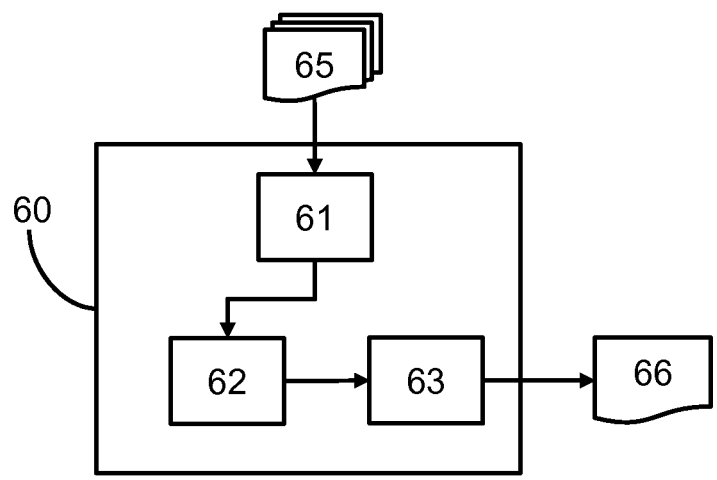
FIG. 6 illustrates a system for monitoring moveable entities within a predetermined area according to an embodiment.

FIG. 6 illustrates a system 60 for monitoring moveable entities within a predetermined area.

The system 60 comprises a stream receiving unit 61 adapted to obtain a stream 65 of real-time location, RTL, information identifying current locations of movable entities within the predetermined area.

The system 60 also comprises a processing unit 62 adapted to process the stream of real-time location information to generate occupancy information of each of a plurality of predetermined zones of the predetermined area.

The system 60 also comprises a occupancy cause identifying unit 63 adapted to process the occupancy information using a machine-learning model to thereby determine one or more occupancy causes 66, each occupancy cause indicating a reason that one or more predetermined zones are occupied by one or more moveable entities, wherein the machine-learning model defines a relationship between occupancy information and occupancy causes.

The present invention may be a system, a method, and/or a computer program product. The computer program product may include a computer readable storage medium (or media) having computer readable program instructions thereon for causing a processor to carry out aspects of the present invention. The computer readable storage medium can therefore be a tangible device that can retain and store instructions for use by an instruction execution device, such as a controller, processor or processing system, for executing a method according to the present invention. Disclosed methods are considered suitable for execution by a computer, and may therefore be computer-implemented methods.

The present invention is described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s) or a module of a system for implementing the specified functions.

In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Variations to the disclosed embodiments can be understood and effected by those skilled in the art in practicing the claimed invention, from a study of the drawings, the dis-

The invention claimed is:

1. A computer-implemented method of monitoring moveable entities within a predetermined area, the method comprising:
obtaining a stream of real-time location, RTL, information identifying current locations of movable entities within the predetermined area;
processing the stream of real-time location information to generate occupancy information of each of a plurality of predetermined zones of the predetermined area; and
processing the occupancy information using a machine-learning model to thereby determine one or more occupancy causes, each occupancy cause indicating the occurrence of a predetermined event within one or more predetermined zones, wherein the machine-learning model defines a relationship between occupancy information and occupancy causes,
wherein the occupancy information comprises a plurality of sequences of occupancy data entries and the step of processing the occupancy information comprises individually processing each sequence of occupancy data using the machine-learning model to thereby determine one or more occupancy causes, and
wherein the plurality of sequences forms a series of sequences, and each of the series of sequences is associated with a period of time that overlaps a period of time associated with an immediately preceding sequence in the series of sequences.

2. The computer-implemented method of claim 1, wherein: the occupancy information indicates a number of moveable entities in each of the plurality of predetermined zones of the predetermined area; and
the machine-learning model defines a relationship between a number of moveable entities within one predetermined zone relative to other predetermined zones and occupancy causes.

3. The computer-implemented method of claim 1, further comprising determining one or more roles of each at least one movable entity, and wherein:
the occupancy information indicates the one or more roles of each movable entity in each of the plurality of predetermined zones of the predetermined area; and
the machine-learning model defines a relationship between the one or more roles of each moveable entity in each predetermined zone and occupancy causes.

4. The computer-implemented method of claim 1, wherein:
the step of processing the stream of real-time location information comprises generating, as the occupancy information, a sequence among the plurality of sequences of occupancy data entries, each occupancy data entry indicating a number of moveable entities within each of the plurality of predetermined zones of the predetermined area at a single point in time; and
each occupancy data entry is associated with a single point in time later than a previous occupancy data in the sequence, so that the overall sequence indicates a number of moveable entities within each of the plurality of predetermined zones over a period of time.

5. The computer-implemented method of claim 4, wherein the machine-learning model defines a relationship between the sequence and one or more occupancy causes.

6. The computer-implemented method of claim 1, further comprising determining one or more roles of each at least one movable entity, wherein the step of generating each sequence of occupancy data entries comprises generating a sequence of occupancy data entries wherein each occupancy data entry indicates a number of moveable entities of each role within each of the plurality of predetermined zones of the predetermined area at a single point in time.

7. The computer-implemented method of claim 1, wherein determining the one or more occupancy causes comprises determining whether a predetermined event has occurred during a time during which the stream of real-time location, RTL, information is provided.

8. A tangible computer readable storage medium having a computer program stored therein, the computer program comprising code which executes the method of claim 1 when said computer program is run on a computer.

9. A system for monitoring moveable entities within a predetermined area, the system comprising:
a stream receiving unit adapted to obtain a stream of real-time location, RTL, information identifying current locations of movable entities within the predetermined area;
a processing unit adapted to process the stream of real-time location information to generate occupancy information of each of a plurality of predetermined zones of the predetermined area; and
an occupancy cause identifying unit adapted to process the occupancy information using a machine-learning model to thereby determine one or more occupancy causes, each occupancy cause indicating the occurrence of a predetermined event within one or more predetermined zones, wherein the machine-learning model defines a relationship between occupancy information and occupancy causes,
wherein the occupancy information comprises a plurality of sequences of occupancy data entries and the step of processing the occupancy information comprises individually processing each sequence of occupancy data using the machine-learning model to thereby determine one or more occupancy causes, and
wherein the plurality of sequences forms a series of sequence, and each of the series of sequences is associated with a period of time that overlaps a period of time associated with an immediately preceding sequence in the series of sequences.

10. The system of claim 9, further comprising a role determining unit adapted to determine one or more roles of each at least one movable entity, wherein:
the occupancy information indicates the one or more roles of each movable entity in each of the plurality of predetermined zones of the predetermined area; and
the machine-learning model defines a relationship between the one or more roles of each moveable entity in each predetermined zone and occupancy causes.

11. The system of claim 9, wherein the processing unit is adapted to processing the stream of real-time location information to generate a sequence among the plurality of sequences of occupancy data entries, each occupancy data entry indicating a number of moveable entities within each of the plurality of predetermined zones of the predetermined area at a single point in time.

12. The system of claim 11, wherein:
the processing unit is adapted to generate the plurality of sequences of occupancy data entries; and
the occupancy cause identifying unit is adapted to individually process each sequence of occupancy data in the plurality of sequences using a machine-learning model to thereby determine one or more occupancy causes.

* * * * *